United States Patent [19]

Schreinemakers

[11] 4,146,963
[45] Apr. 3, 1979

[54] DENTAL IMPRESSION TRAY

[76] Inventor: Josephus Schreinemakers, Piuslaan 130, Eindhoven, Netherlands

[21] Appl. No.: 733,948

[22] Filed: Oct. 19, 1976

[30] Foreign Application Priority Data

Oct. 21, 1975 [NL] Netherlands ............... 7512346

[51] Int. Cl.$^2$ .............................................. A61C 9/00
[52] U.S. Cl. ............................................. 32/17
[58] Field of Search .................................. 32/17, 18, 19

[56] References Cited

U.S. PATENT DOCUMENTS

| 1,445,499 | 2/1923 | Douglass | 32/17 |
| 1,505,862 | 8/1924 | Carroll, Sr. | 32/17 |
| 2,529,429 | 11/1950 | Spiro | 32/17 |
| 3,473,225 | 10/1969 | Deuschle et al. | 32/17 |

FOREIGN PATENT DOCUMENTS

| 928907 | 5/1955 | Fed. Rep. of Germany | 32/19 |
| 313284 | 6/1929 | United Kingdom | 32/17 |
| 855148 | 11/1960 | United Kingdom | 32/19 |

*Primary Examiner*—Russell R. Kinsey
*Assistant Examiner*—John J. Wilson
*Attorney, Agent, or Firm*—Haseltine, Lake & Waters

[57] ABSTRACT

A perforated tray for taking an impression of an upper or a lower jaw, which may be dentulous or edentulous. In this tray all perforations are shaped as elongated slits. Further the slits may extend at least approximately transversely to the vestibular outline of the tray when viewed from above or from below. The part of the tray, which covers in situ the top of the crest of the jaw, or the masticatory surfaces of the teeth, may be left unperforated. In a tray for taking an impression of an upper jaw, the part of the tray which covers in situ the torus palatinus lying in the center of the palate, may be left unperforated.

2 Claims, 4 Drawing Figures

DENTAL IMPRESSION TRAY

BACKGROUND OF THE INVENTION

Field of the Invention

The invention relates to a perforated tray for taking an impression of an upper or a lower jaw which may be dentulous or edentulous.

Prior Art

Known trays are in general provided with small, round or approximately square perforations divided over the entire surface of the tray. During the taking of an impression, the impression material flows through these perforations to the non-operative surface of the tray, in order to obtain a mechaical connection between the impression material and the frame of the tray after the setting of the impression material, so that a disconnection of the impression material from the operative inner surface of the tray is prevented.

However, this known tray shows the disadvantage that due to the small dimensions of the perforations and subsequently of the cross-section of the impression material set in these perforations, the connection between the impression material, which has been pressed through the perforations and the impression material on the inner surface of the tray, which holds the real replica of the object of which the impression has to be taken, is comparatively weak and may easily be broken under the influence of local tensile forces.

Additionally, the known trays are comparatively difficult to clean due to the small dimensions of the perforations.

SUMMARY OF THE INVENTION

It is an object of the present invention to provide a tray of the type as mentioned, wherein the above disadvantages are overcome in a simple, but nevertheless effective manner.

To this end, the tray according to the invention is characterized in that all perforations are shaped as elongated slits.

In this connection the expression "an elongated slit" is intended to indicate a slit having a longitudinal dimension which is at least three times and preferably even considerably more than five times larger than its width.

Due to the fact that the cross-section of each elongated slit of the tray according to the invention is much larger than the cross-section of a small perforation of the known tray, the cross-section of the impression material set in this slit is also considerably larger than the cross-section of the impression material set in the small perforation. As a consequence, according to the invention, a much stronger connection between the impression material passed through the slits and the impression material on the inner surface of the tray is obtained, so that a considerably larger resistance against a disconnection of the impression from the frame of the tray is experienced when local tensile forces occur. Additionally, the elongated slits are easier to clean than the small round perforations of the known trays.

Preferbly, the slits extend at least approximately transversely to the vestibular outline of the tray when viewed from above or from below, while in a tray for taking an impression of the lower jaw the slits preferably also extend at least approximately transversely to the lingual outline of the tray when viewed from above.

Further it is considered advantageous for the width of the slits to increase from the operative inner surface to the non-operative outer surface of the tray. In this manner, the connection between the impression material and the frame of the tray is still further increased.

A very important embodiment of the tray according to the invention is characterized in that the part of the tray which covers in situ the top of the crest of the jaw, or the masticatory surfaces of the teeth, is left unperforated.

This completely closed part of the tray causes an intensified lateral flow of the impression material mainly in a direction which is approximately parallel to the unperforated closed surface of the tray. In this manner, possible inclusions of air between the impression material, on the one hand, and the object to be impressed, on the other hand, are carried off laterally and are finally removed through the slits. In this way, it is achieved that the top or summit part of the crest of the jaw, or the masticatory surfaces of the teeth, are reproduced very closely in the impression material.

Additionally, in a tray for taking an impression of an upper jaw the part of the tray which covers in situ the torus palatinus, which lies in the center of the palate, is left unperforated.

Due to this latter closed part of the tray, which in general has an approximately elliptic outline, again an intensified lateral flow of the impression material is obtained. Thus, possible inclusions of air between the impression material and the object to be impressed are again carried off and it is achieved that the center of the palate is very closely reproduced in the impression material.

The bridges between successive slits as well cause a similar intensified fow of the impression material, so that possible inclusions of air between the impression material and the object to be impressed will be removed through the slits in an effective manner, which, of course, extremely favorably influences the quality of the impression.

The areas of the crest of the jaw, or of the masticatory surfaces, and the area of the torus palatinus are very accessible for inclusions of air. For this reason, these are the very areas where the known trays show a frequent inclusion of air between the impression material and the object to be impressed. In the known trays, the parts corresponding with these areas are always perforated.

The operation of the trays according to the invention is entirely different from the operation of the known trays which are perforated over their entire surface and whereby, due to the overall presence of passages for the impression material, a flow of the impression material parallel to the surface of the tray will not or insufficiently occur. In contrast according to the invention, the presence of the slits and their specific course will locally strongly enhance the escape of impression material, and the impression material will be forced at other places to flow in a lateral direction, viz. in a direction towards the slits. This causes a strong flow in the impression material by which any inclusion of air is prevented.

The fact that the above described parts of the tray are left unperforated is made possible by the slit-shape of the perforations, which, because of their larger passage cross-section, compensate the unperforated parts of the tray.

BRIEF DESCRIPTION OF THE DRAWINGS

The invention will hereafter be elucidated with reference to the drawings, which show several embodiments of trays according to the invention, by way of example.

DESCRIPTION OF PREFERRED EMBODIMENTS

Figure 2:
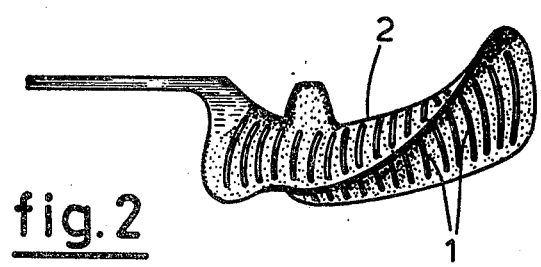
FIG. 2 is a side view of the tray according to FIG. 1.
Figure 1:
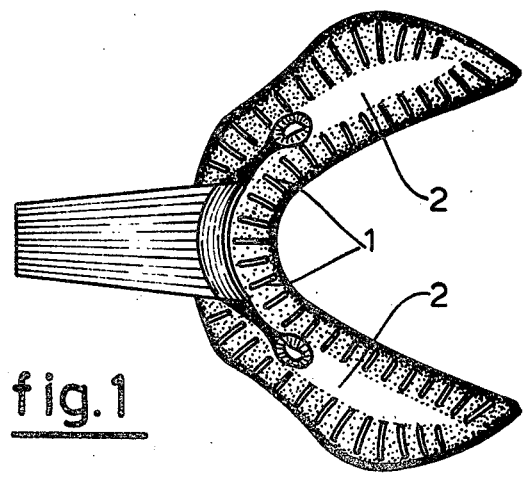
FIG. 1 is a plan view of an embodiment of a tray according to the invention for taking an impression of an edentulous lower jaw.

FIGS. 1 and 2 show an embodiment of a tray for taking an impression of an edentulous lower jaw, by way of example. This tray is provided with elongated slits 1, which, when viewed from above, extend at least approximately transversely to the vestibular outline of the tray as well as to the lingual outline of the tray. The width of the slits 1 may increase from the operative inner surface of the tray to the non-operative outer surface of the tray and may, for instance, amount to 1.5 mm on the operative side of the tray and 2 mm on the non-operative side of the tray. The part of the tray 2, which in situ covers the top of the crest of the jaw, is not perforated.

Figure 4:
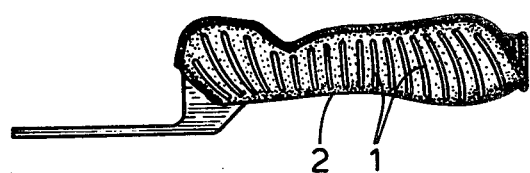
FIG. 4 is a side view of the tray according to FIG. 3.
Figure 3:
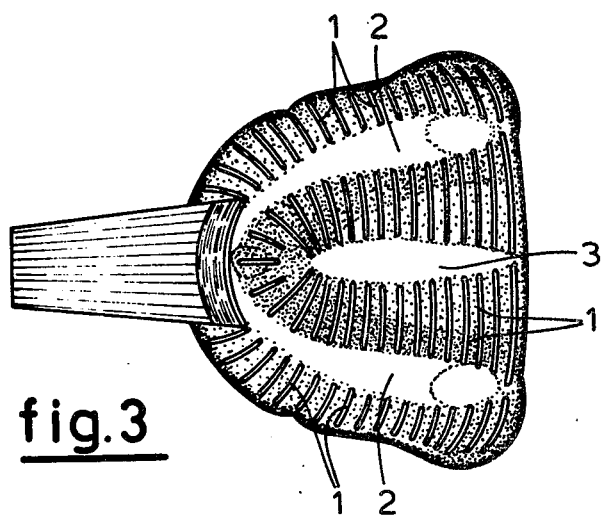
FIG. 3 is a view from below of a embodiment of a tray according to the invention for taking an impression of an edentulous upper jaw.

FIGS. 3 and 4 show a tray for taking an impression of an edentulous upper jaw. This tray is again provided with elongated slits 1. These slits 1 extend at least approximately transversely to the outline of the tray when viewed from below. In this tray again the width of the slits 1 may increase from the operative inner surface to the non-operative surface of the tray.

In this tray not only the part 2 which in situ covers the top of the crest of the jaw, but also the part 3 of the tray, which in situ covers the torus palatinus lying in the center of the palate and having a somewhat ellipital outline (FIG. 3) has been left unperforated.

The application of the elongated slits 1 in the trays according to the invention results in an extremely strong adhesion of the impression material to the tray, which can effectively resist local tensile forces on the impression material.

Further, the application of the unperforated closed parts 2, 3 of the tray results in the elimination of air inclusions between the impression material and the object to be impressed, so that an impression will be obtained, which meets very high demands.

The invention is not restricted to the embodiments shown in the drawings by way of example, which may be varied in different ways within the scope of the appended claims.

For instance the invention also comprises trays for taking an impression of a dentulous upper or lower jaw. The part of the tray corresponding with the part 2 of the tray, which in the latter case in situ covers the masticatory surfaces of the teeth, will be left completely unperforated.

I claim:

1. A perforated tray for taking an impression of a lower jaw, which may be dentulous or edentulous, said tray being provided with perforations which are shaped solely as elongated slits, which slits extend at least approximately transversely to the vestibular outline and to the lingual outline of the tray when viewed from above, the part of the tray, which covers in situ the top of the crest of the jaw, or the masticatory surfaces of the teeth, being left unperforated, two distinct rows of said perforations being formed on opposite sides of said unperforated portion of the tray, said slits being oriented on opposite sides of the unperforated regions to enhance escape of impression material and promote flow from the unperforated regions laterally toward the slits whereby inclusion of air is minimized, said slits having a width which increases from the operative inner surface to the non-operative outer surface of the tray.

2. A perforated tray for taking an impression of an upper jaw, which may be dentulous or edentulous, said tray being provided with perforations which are shaped solely as elongated slits, which slits extend at least approximately transversely to the vestibular outline of the tray when viewed from below, a first portion of the tray which covers in situ the top of the crest of the jaw, or the masticatory surfaces of the teeth, being left unperforated, a second portion of the tray, which covers in situ the torus palatinus lying in the center of the palate also being left unperforated, said second portion having an approximately elliptical outline, two distinct rows of said perforations being formed on opposite sides of said first unperforated portion of the tray, one of said rows surrounding the second unperforated portion, said slits being oriented on opposite sides of the unperforated regions to enhance escape of impression material and promote flow from the unperforated regions laterally toward the slits whereby inclusion of air is minimized, said slits having a width which increases from the operative inner surface to the non-operative outer surface of the tray.

* * * * *